US012805931B2

(12) United States Patent
Govari et al.

(10) Patent No.: US 12,805,931 B2
(45) Date of Patent: *Nov. 24, 2026

(54) REFERENCE ELECTRODE DEDICATED TO CATHETER TISSUE PROXIMITY ESTIMATION

(71) Applicant: BIOSENSE WEBSTER (ISRAEL) LTD., Yokneam (IL)

(72) Inventors: Assaf Govari, Haifa (IL); Vadim Gliner, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 291 days.

This patent is subject to a terminal disclaimer.

(21) Appl. No.: 18/530,268

(22) Filed: Dec. 6, 2023

(65) Prior Publication Data

US 2025/0186109 A1 Jun. 12, 2025

(51) Int. Cl.
*A61B 18/14* (2006.01)
*A61B 18/00* (2006.01)

(52) U.S. Cl.
CPC .. *A61B 18/1492* (2013.01); *A61B 2018/0022* (2013.01); *A61B 2018/00267* (2013.01);
(Continued)

(58) Field of Classification Search
CPC ........ A61B 18/1492; A61B 2018/0022; A61B 2018/00267; A61B 2018/00351;
(Continued)

(56) References Cited

U.S. PATENT DOCUMENTS 5,391,199 A 2/1995 Ben-Haim
5,443,489 A 8/1995 Ben Haim
(Continued)

FOREIGN PATENT DOCUMENTS

CN 115363746 A * 11/2022 ......... A61B 18/1492
EP 3053517 A1 8/2016
(Continued)

OTHER PUBLICATIONS

Translation of CN 115363746A (Year: 2022).*
Extended European Search Report, received for European Application No. 24217631.1, mailed on Apr. 24, 2025, 11 pages.

*Primary Examiner* — Beverly M Flanagan
(74) *Attorney, Agent, or Firm* — FBT GIBBONS LLP

(57) ABSTRACT

A catheter includes a shaft having a distal-end and an expandable distal-end assembly configured for insertion into a cavity of an organ of a patient. The expanded assembly defines an inner volume and includes (i) a proximal base section configured to couple the assembly to the shaft's distal-end, (ii) a plurality of functional electrodes that are at least partially external to the inner volume and configured to be placed in contact with wall tissue of the cavity, and (iii) a reference ring electrode located on the proximal base section of the assembly externally to the inner volume, wherein the reference ring electrode is selectively positioned outside of the inner volume at the base section, and wherein the reference ring electrode is configured to be coupled with each of the plurality of functional electrodes for generating an electric field between each of the plurality of functional electrodes and the ring electrode.

20 Claims, 3 Drawing Sheets

(52) U.S. Cl.
CPC ............... *A61B 2018/00351* (2013.01); *A61B 2018/00577* (2013.01); *A61B 2018/00642* (2013.01); *A61B 2018/00666* (2013.01); *A61B 2018/00875* (2013.01); *A61B 2018/1407* (2013.01); *A61B 2018/1467* (2013.01)

(58) Field of Classification Search
CPC ........... A61B 2018/00577; A61B 2018/00642; A61B 2018/00666; A61B 2018/00875; A61B 2018/1407; A61B 2018/1467; A61B 2090/0427; A61B 2090/065; A61B 5/287; A61B 5/367
USPC ............................................................ 606/41
See application file for complete search history.

(56) References Cited

U.S. PATENT DOCUMENTS

| | | | |
|---|---|---|---|
| 5,558,091 | A | 9/1996 | Acker |
| 6,172,499 | B1 | 1/2001 | Ashe |
| 6,239,724 | B1 | 5/2001 | Doron |
| 6,332,089 | B1 | 12/2001 | Acker |
| 6,484,118 | B1 | 11/2002 | Govari |
| 6,618,612 | B1 | 9/2003 | Acker |
| 6,690,963 | B2 | 2/2004 | Ben Haim |
| 6,788,967 | B2 | 9/2004 | Ben Haim |
| 6,892,091 | B1 | 5/2005 | Ben Haim |
| 7,536,218 | B2 | 5/2009 | Govari |
| 7,756,576 | B2 | 7/2010 | Levin |
| 7,848,787 | B2 | 12/2010 | Osadchy |
| 7,869,865 | B2 | 1/2011 | Govari |
| 8,456,182 | B2 | 6/2013 | Bar-Tal |
| 2021/0369132 | A1 | 12/2021 | Van Niekerk et al. |
| 2023/0112251 | A1 | 4/2023 | Govari |

FOREIGN PATENT DOCUMENTS

| | | | |
|---|---|---|---|
| EP | 3603493 | A2 | 2/2020 |
| EP | 3785656 | A1 | 3/2021 |
| EP | 4162866 | A1 | 4/2023 |

* cited by examiner

REFERENCE ELECTRODE DEDICATED TO CATHETER TISSUE PROXIMITY ESTIMATION

FIELD OF THE DISCLOSURE

The present disclosure relates generally to invasive medical probes, and particularly to estimation of proximity of catheters to tissue.

BACKGROUND OF THE DISCLOSURE

Techniques to estimate the proximity of an electrode of a catheter to tissue were previously proposed in the patent literature. For example, U.S. Patent Application Publication 2023/0112251 describes a system including a catheter and a processor. The catheter includes a distal-end assembly coupled to a distal end of a shaft for insertion into a cavity of an organ of a patient, the distal-end assembly including (i) one or more functional electrodes configured to be placed in contact with wall tissue of the cavity and (ii) a reference electrode configured to be placed in the cavity but not in contact with the wall tissue. The reference electrode is disclosed as an electrode that is positioned within an inner volume defined by the distal-end assembly. Selectively placing the reference electrode within that inner volume provides distancing the reference electrode from the tissue wall. The processor is configured to (i) estimate one or more impedances between one or more of the functional electrodes and the reference electrode, and (ii) based on the impedances, determine, for at least a functional electrode from among the one or more functional electrodes, whether the functional electrode is in physical contact with the wall tissue.

The present disclosure will be more fully understood from the following detailed description of the examples thereof, taken together with the drawings, in which:

DETAILED DESCRIPTION OF EXAMPLES

Overview

Figure 1:
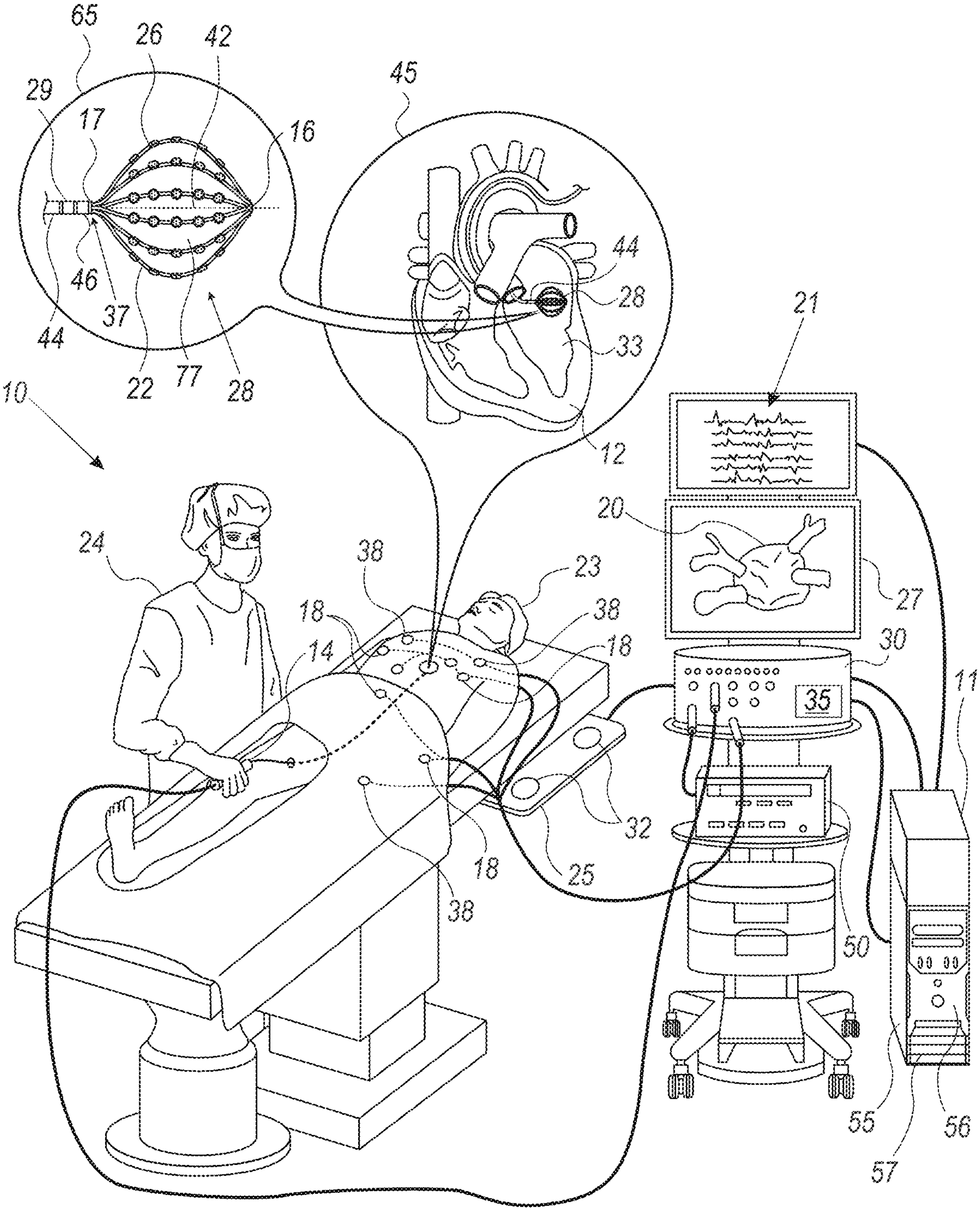
FIG. 1 is a schematic, pictorial illustration of a catheter-based electroanatomical (EA) mapping and ablation system, in accordance with an example of the present disclosure.

Wall tissue of a cavity of an organ of a patient, such as a cardiac chamber, can be electroanatomically mapped and/or ablated using a catheter having multiple functional electrodes fitted at an expandable distal-end assembly of the catheter. In a mapping and/or ablation procedure in a cardiac chamber, the physician may manipulate an expanded distal-end assembly to have the electrodes contact chamber walls to acquire and/or apply electrical signals.

The quality of electrical mapping and/or ablation depends on the proximity of the functional electrodes to the cavity wall tissue (also called in the disclosure "tissue proximity indication (TPI)"). A proximity scale may use arbitrary units (e.g., an index ranging from 1 to 10) or can be given in physical units of distance.

A processor can be configured to estimate the proximity using calibrated proximity data by translating impedance to electrode-tissue proximity. One way to calculate the TPI is to: (i) identify from the monitored imbalances a range of the lowest and highest values recorded over time, (ii) normalize the monitored impedances according to the range, and (iii) relate the normalized range to a scale of TPI.

Another option is that TPI is a binary value, e.g., 0 for no touch, and 1 for touch. One way to calculate the binary TPI is to: (i) identify from the monitored imbalances a range of the lowest and highest values recorded over time, (ii) set a threshold according to the range, and (iii) define a corresponding normalized threshold according to the normalized range of TPI. For example, a normalized threshold value of 0.7 above which the reported TPI is 1, and below, zero.

The system measures an impedance between a pair of electrodes, one of which is a reference electrode that is in the blood pool and the other a functional electrode. Based on this measurement a processor runs an algorithm to determine the proximity of the functional electrode to the tissue. Minimal impedance occurs when the functional electrode is well within the blood pool of a cardiac chamber, while maximal impedance occurs when the functional electrode is in full contact, e.g., engagement with a threshold pressure. The impedance reading is continuous between these two limits.

In some known methods, a reference electrode is positioned within an inner volume of an expandable distal assembly as described herein above. The inventors have found that improved sensitivity may be achieved by directing a larger portion of the electric field outwardly across the volume that may potentially include a portion of the tissue wall. To this end, they propose to locate a reference electrode externally to the inner volume of the expandable distal assembly at a location where the reference electrode will be spaced away from any contact with tissue.

Examples of the present disclosure that are described herein provide a ring electrode, selectively positioned at a base of the expandable assembly and in close proximity to the expandable portion of the distal assembly. The base of the expandable assembly, being part of the assembly, is the element to which the assembly is coupled to a distal end of a shaft of the catheter, i.e., the ring reference electrode is distal to the shaft. Since the ring reference electrode is at the base of the expandable assembly, it typically does not touch the tissue wall while the expandable assembly is in an expanded state. Further to that, the ring reference electrode diameter is about 2-5 mm in diameter while the distal end assembly in its expanded state is sphere-like with a diameter of about 20-30 mm. Due to this significant difference in diameter, positioning the reference electrode at the base of the distal end assembly has the assembly acting as a spacer that spaces the reference electrode away from the tissue.

The path of the electric potential between such a ring reference electrode and a functional electrode is sensitive to tissue proximity, as both the plurality of functional electrodes and the reference ring electrode are external to an inner volume defined by the expandable assembly. Proximity is therefore based on monitoring an increase in impedance over time for each functional electrode.

Figure 2:
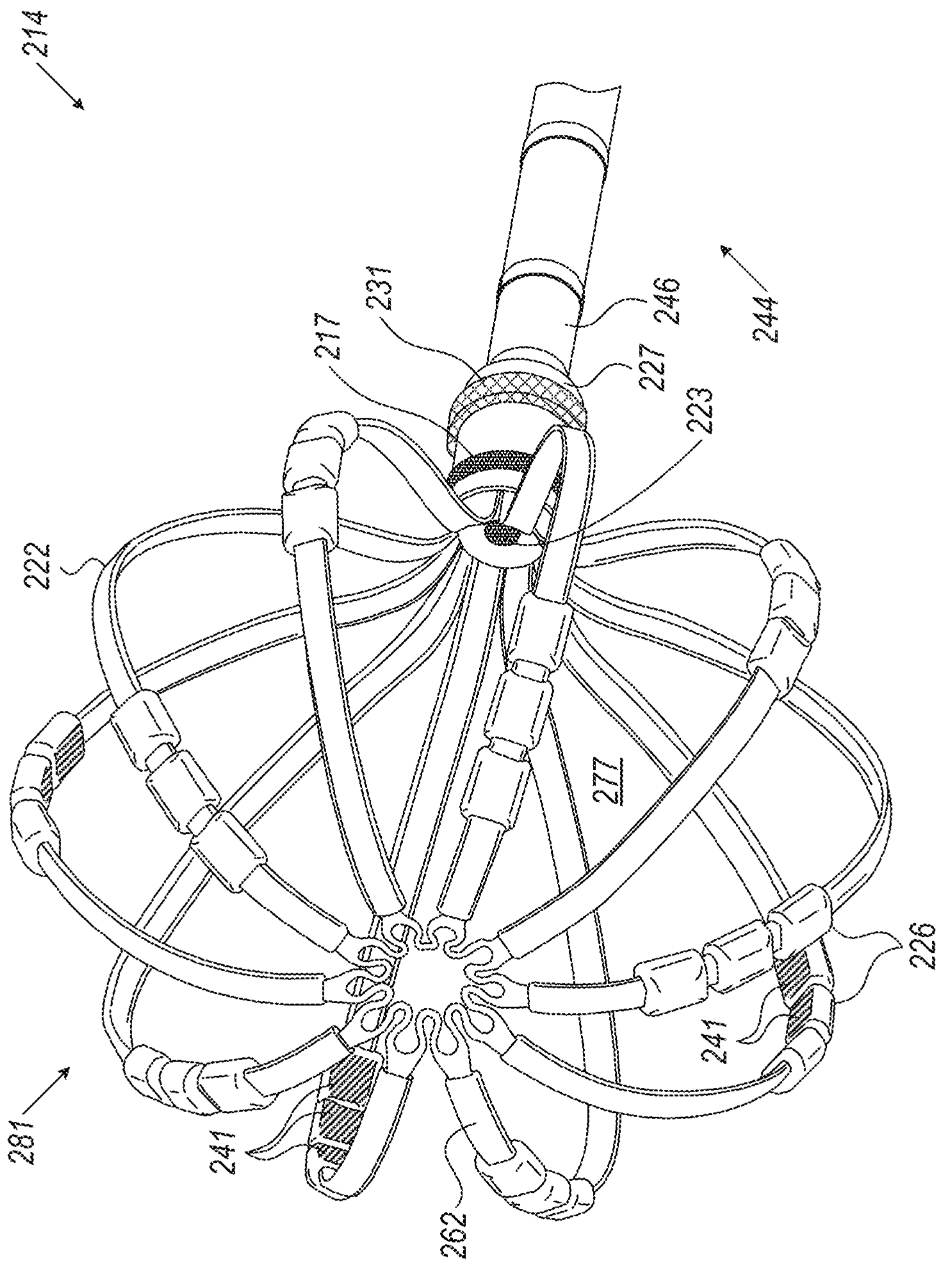
FIG. 2 is a schematic, pictorial illustration of a basket assembly configured to electrically sense proximity of a functional electrode to a cavity wall tissue, in accordance with an example of the present disclosure.

In addition, and primarily for basket catheters, the electric field path through the inner-facing side of the functional electrodes can be eliminated and/or reduced by coating the inner-facing side of the spline with an insulating coating, as described in FIG. 2.

In an example, an additional guard ring protrudes further than the reference ring electrode, and is configured to act as a spacer that blocks contact between the reference ring and tissue wall. This way the guard ring reduces instances of touch, e.g., near a ridge of a cardiac chamber anatomy.

Since, in some examples, the distal end assembly is essentially one piece made from a nitinol tube, the base section, as a proximal section of the distal end assembly, is electrically conductive. In these examples, the reference ring electrode is electrically insulated from the nitinol base.

Finally, despite the efforts described above, sometimes the reference electrode may touch tissue. This can be identified by comparing the electrical signals from all of the functional electrodes. If all of the signals from all of the functional electrodes signify touch (e.g., all simultaneously show an increase in impedance), it is most likely caused by the reference electrode touching tissue, since some functional electrodes should always be immersed in a blood pool. Therefore, in this case, the system discards this reading.

System Description

FIG. 1 is a schematic, pictorial illustration of a catheter-based electroanatomical (EA) mapping and ablation system 10, in accordance with an example of the present disclosure. System 10 is configured to determine, e.g., prior to performing diagnostics and/or ablation, whether a given functional electrode 26 of a plurality of functional electrodes 26 of a basket catheter 14 has sufficient contact with (or proximity to) tissue, or is immersed in blood pool 33 of a cardiac chamber.

System 10 includes one or more catheters which are percutaneously inserted, by physician 24, through the patient's vascular system into a chamber or vascular structure of a heart 12. Typically, a delivery sheath catheter is inserted into the left or right atrium near a desired location in heart 12. Thereafter, one or more catheters, in turn, can be inserted into the delivery sheath catheter to arrive at the desired location. The one or more catheters may include catheters dedicated for sensing intracardiac electrogram (IEGM) signals, catheters dedicated to ablating and/or catheters dedicated to both sensing and ablating. An example basket catheter 14 that is configured for sensing IEGM is illustrated herein. As seen in inset 45, physician 24 brings a basket type of expandable distal-end assembly 28 (also called hereinafter "expandable distal-end assembly 28") fitted on a shaft 44 of catheter 14 into contact with the heart wall for sensing a target site in heart 12. For ablation, physician 24 similarly brings the distal end of an ablation catheter to a target site for ablating.

As seen in inset 65, catheter 14 is an exemplary catheter that includes one, and preferably multiple, functional electrodes 26 optionally distributed over a plurality of splines 22 at expandable distal-end assembly 28 and configured to sense IEGM signals. Catheter 14 additionally includes a proximal position sensor 29 (e.g., TAS 29 comprising three EMCs) embedded in a distal end 46 of shaft 44 near expandable distal end assembly 28, to track the position of the distal end of expandable distal end assembly 28. Optionally, and preferably, position sensor 29 is a magnetic-based position sensor that includes magnetic coils for sensing three-dimensional (3D) position. Distal end 46 of shaft 44 may comprise an amplifying circuit configured to amplify the output from the three EMCs of sensor 29.

Magnetic position sensor 29 is operated together with an external location pad 25 that includes a plurality of magnetic coils 32 configured to generate magnetic fields in a predefined working volume. Using the operation with external location pad 25 (each EMC using a different frequency), the processor can determine the position of each EMC 29 on a coordinate system of the position tracking system.

Details of the magnetic-based position sensing technology are described in U.S. Pat. Nos. 5,391,199; 5,443,489; 5,558,091; 6,172,499; 6,239,724; 6,332,089; 6,484,118; 6,618,612; 6,690,963; 6,788,967; 6,892,091.

System 10 includes one or more electrode patches 38 positioned for skin contact on patient 23 to establish a location reference for location pad 25 as well as impedance-based tracking of functional electrodes 26. For impedance-based tracking, electrical current is directed toward electrodes 26 and sensed at electrode skin patches 38, such that the location of each electrode can be triangulated via electrode patches 38. Real-time orientation of expandable distal end assembly 28 of catheter 14 can be calculated from tracked locations of electrodes 26. This relative orientation is manifested by an angle formed between distal end 46 and a longitudinal axis 42 of expandable assembly 28 (to a distal edge 16 of the assembly).

Details of the impedance-based location tracking technology are described in U.S. Pat. Nos. 7,536,218; 7,756,576; 7,848,787; 7,869,865; and 8,456,182.

Catheter 14 is configured to acquire electrical signals indicative of proximity of any given functional electrode 26 to the wall tissue of heart 12. To this end, a signal generator 35 is configured to generate an AC signal between a reference ring electrode 17 and each of the functional electrodes 26. The processor measures corresponding impedances between each functional electrode 26 and reference ring electrode 17 located on a base 37 of the expandable distal-end assembly 28 externally to an inner volume 77 defined by the splines of assembly 28.

Having the electrical path between each functional electrode 26 and reference ring electrode 17 to assembly 28 improves the sensitivity of the measurement to tissue proximity. Reference ring electrode 17 is positioned on a base of the assembly 28 in a place that avoids contact with the tissue wall while the distal end assembly 28 is in an expanded state, as further described in FIG. 2.

A recorder 11 displays electrograms 21 captured with body surface ECG electrodes 18 and intracardiac electrograms (IEGM) captured with functional electrodes 26 of catheter 14. Recorder 11 may include pacing capability for pacing the heart rhythm and/or may be electrically connected to a standalone pacer.

System 10 may include an ablation energy generator 50 that is adapted to conduct ablative energy to a subset of the plurality of electrodes 26 at the distal assembly 28 of catheter 14 configured for ablating. Energy produced by ablation energy generator 50 may include, but is not limited to, radiofrequency (RF) energy or pulsed-field ablation (PFA) energy, including monopolar or bipolar high-voltage DC pulses that may be used to effect irreversible electroporation (IRE), or combinations thereof.

Patient interface unit (PIU) 30 is configured to establish electrical communication between catheters, electrophysiological equipment, power supply and a workstation 55 for controlling the operation of system 10. Electrophysiological equipment of system 10 may include, for example, multiple catheters, location pad 25, body surface ECG electrodes 18, electrode patches 38, ablation energy generator 50, and recorder 11. Optionally, and preferably, PIU 30 additionally includes processing capability for implementing real-time computations of catheter locations and for performing ECG calculations.

Workstation 55 includes memory 57, processor unit 56 with memory or storage with appropriate operating software loaded therein, and user interface capability. Workstation 55 may provide multiple functions, optionally including (i) modeling endocardial anatomy in three-dimensions (3D) and rendering the model or anatomical map 20 for display on a display device 27, (ii) displaying on display device 27 activation sequences (or other data) compiled from recorded electrograms 21 in representative visual indicia or imagery superimposed on the rendered anatomical map 20, (iii) displaying real-time location and orientation of multiple catheters within the heart chamber, and (iv) displaying on display device 27 sites of interest such as places where ablation energy has been applied. One commercial product embodying elements of system 10 is available as the CARTO™ 3 System, available from Biosense Webster, Inc., 31A Technology Drive, Irvine, CA 92618.

While FIG. 1 describes a basket assembly, the disclosed technique can be applied, mutatis mutandis, to an expandable balloon assembly having an expandable membrane, wherein the functional electrodes are disposed over the membrane.

Estimation of Touch Proximity (TP) of a Functional Electrode of Expandable Assembly FIG. 2 is a schematic, pictorial illustration of a basket catheter assembly 281 configured for electrical measurement of the proximity of a functional electrode 226 to cavity wall tissue, in accordance with an example of the present disclosure. Basket assembly 281 can be used to implement basket assembly 28 of FIG. 1 above. As seen, assembly 281 is part of a catheter 214 further comprising a shaft 244 having a distal end 246. Distal-end assembly 228 includes a proximal base 227 configured to couple the assembly to a distal end 246 of the shaft 244.

Basket assembly 281 is realized as an expandable frame comprising multiple splines 222, wherein the functional electrodes 226 are coupled to the splines. Splines 22 are each electrically insulated from the environment over most of their area by an insulation layer 262.

When expanded, as shown in FIG. 2, the expandable distal-end assembly 281 defines an inner volume 277. At the base of the assembly inside volume 277, a far-field electrode 223 is used to remove far-field signals from IEGM signals acquired by electrodes 226.

The plurality of functional electrodes 226 are at least partially external to the inner volume and are configured to be placed in contact with wall tissue of the cavity. A reference ring electrode 217 (such as ring electrode 17 of FIG. 1), is located on proximal base 227 of the expandable distal-end assembly 281 and externally to the inner volume 277. The position of the ring shaped electrode 217 over base 227 is set such to avoid contact with tissue wall while the distal end assembly 281 is in an expanded state.

In the example of FIG. 2, reference ring electrode 217 is a ring fitted on an external perimeter of the proximal base section 227. Reference ring electrode 217 may be disposed over an insulating layer (not shown), for example when base section 227 is electrically conductive (e.g., made of nitinol).

The proximal base section 227 further comprises a mechanical guard ring 231 that protrudes outwards from the proximal base, i.e., further than reference electrode 217, to prevent reference electrode 217 from contact with wall tissue.

Processor 56 estimates the proximity of a given electrode 226 to wall tissue (wall tissue not shown) based on impedance signals between electrodes 226 and reference electrode 217. The processor may use the impedance value itself or an increase in the impedance value relative to a baseline impedance measured when both electrodes are deep inside a pool of blood.

Further improvement of the measurement accuracy can be achieved by applying inner electrical insulation coating 241 to electrode 226 so that the electrode portion in the blood is minimized upon contact with tissue. Coating 241 may be a type of polymer or an additional dielectric layer (e.g., silicon nitride).

While FIG. 2 describes a basket assembly, the disclosed technique can be applied, mutatis mutandis, to an expandable balloon assembly having an expandable membrane, wherein the functional electrodes are disposed over the membrane.

Figure 3:
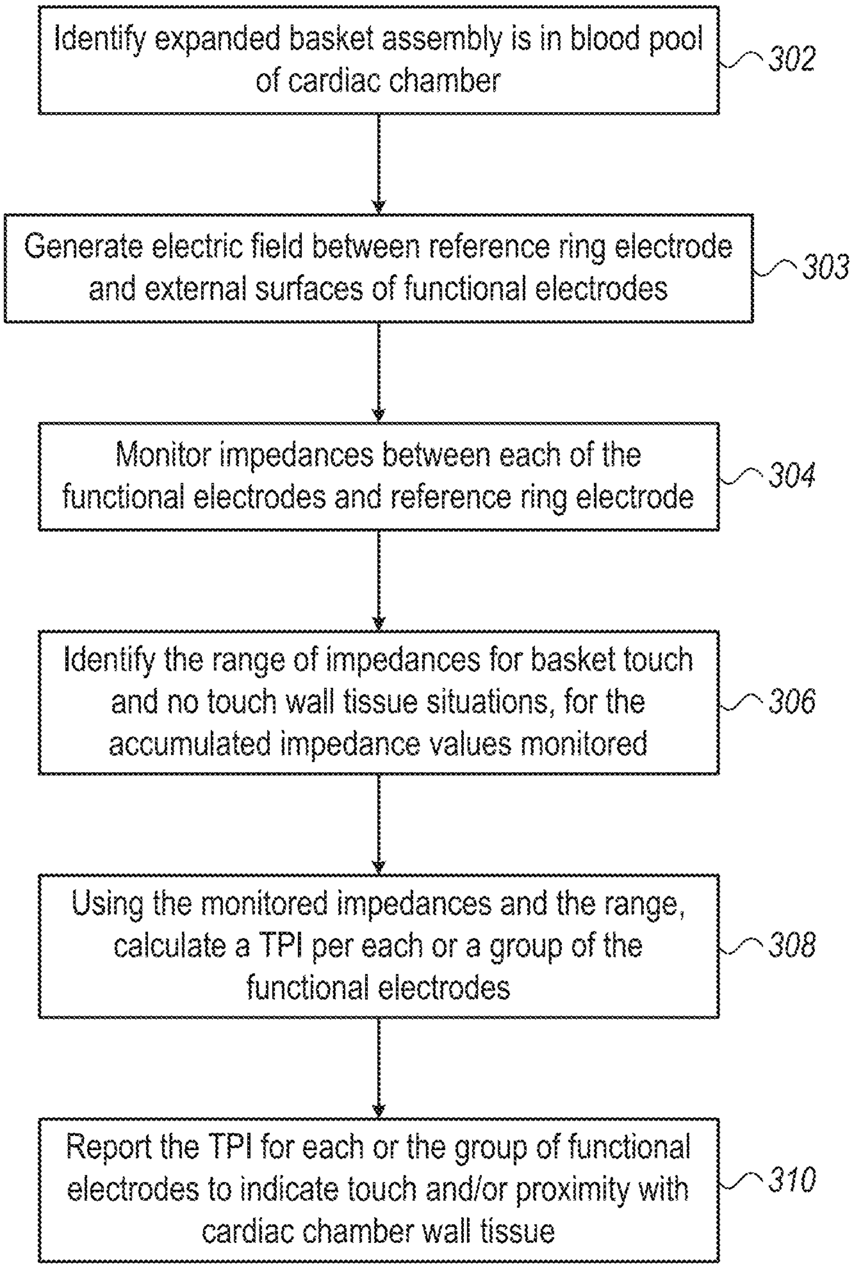
FIG. 3 is a flow chart that schematically illustrates a method and algorithm to estimate proximity of a functional electrode to a cavity wall tissue, in accordance with an example of the present disclosure.

A Method for Estimating Touch Proximity (TP) of an Electrode of an Expandable Assembly FIG. 3 is a flow chart that schematically illustrates a method and algorithm to estimate proximity of a functional electrode to cavity wall tissue, in accordance with an example of the present disclosure. The algorithm, according to the present embodiment, carries out a process that begins with identifying that the expanded basket assembly 281 is in a blood pool 33 inside a cardiac cavity of heart 12, at a basket baseline positioning step 302. This identification can be done using fluoroscopy or contact force sensing to verify no mechanical interaction of basket assembly 281 with the cardiac chamber's wall tissue occurs at least in part of the time.

At electric field generation step 303, the signal generator 35 generates an AC electric field between reference ring electrode 217 and an external surface of each of the functional electrodes 226.

Then, at baseline impedances monitoring step 304, system 10 monitors impedances between each of functional electrodes 226 and reference ring electrode 217.

At impedance range identification step 306, as the basket occasionally contacts cavity wall tissue, the processor identifies the range of impedances for touch and no touch for the accumulated values monitored. The range can be determined from a conglomerate output from all the functional electrodes 226. Clinically, at this stage or later, the physician 24 may further attempt to bring at least a subset of functional electrodes 226 into contact with tissue, e.g., over an entire lateral circumference of assembly 281, as is done in pulmonary vein isolation procedures to treat atrial fibrillation.

Using the monitored impedance and the identified range of such, the processor calculates a TPI per each functional electrode or a group of such electrodes, at TPI calculation step 308. One way to calculate the TPI is to normalize the impedance measurements to a range detected by finding the lowest and highest impedance values recorded over time, and by relating (e.g., translating) the normalized range to a scale of TPI.

Finally, at TPI reporting step 310, system 10 reports the TPI for each or a group of functional electrodes 226 to indicate touch and/or proximity with the cardiac chamber wall tissue of these functional electrodes.

The example flow chart shown in FIG. 3 is chosen purely for the sake of conceptual clarity. The present embodiment also comprises additional steps of the algorithm, such as acquiring intra-cardiac electrocardiograms, which have been omitted from the disclosure herein purposely to provide a more simplified flow chart. In addition, other steps, such as temperature measurements and applying irrigation, are omitted for clarity of presentation.

EXAMPLES

Example 1

A catheter (14) includes a shaft (44) and an expandable distal-end assembly (28). The shaft has a distal end (44) configured for insertion into a cavity of an organ (12) of a patient (23). The expandable distal-end assembly (28), when expanded, defines an inner volume (77), the distal-end assembly (28) comprising (i) a proximal base section (37) configured to couple the distal-end assembly (28) to a distal end (46) of the shaft (44), (ii) a plurality of functional electrodes (26) that are at least partially external to the inner volume (77) and are configured to be placed in contact with wall tissue of the cavity, and (iii) a reference ring electrode (17) located on the proximal base section (37) of the distal-end assembly (28) externally to the inner volume (77), wherein the reference ring electrode (17) is selectively positioned outside of the inner volume (77) at the base section of the distal-end assembly, and wherein the reference ring electrode (17) is configured to be coupled with each of the plurality of functional electrodes (26) for generating an electric field between each of the plurality of functional electrodes (26) and the ring electrode (17).

Example 2

The catheter (14) according to example 1, wherein the reference ring electrode (17) is fitted on an external perimeter of the proximal base section (37), and wherein the reference ring electrode (17) is electrically insulated from the base section (37).

Example 3

The catheter (14) according to any of examples 1 and 2, wherein the distal-end assembly (28) is a basket assembly (281) having an expandable frame comprising multiple splines (22), and wherein the functional electrodes (26) are coupled to the splines (22).

Example 4

The catheter (14, 214) according to any of examples 1 through 3, and comprising a far-field electrode (223) located within the inner volume (77, 277).

Example 5

The catheter (14) according to any of examples 1 through 3, wherein the distal-end assembly is a balloon assembly having an expandable membrane, and wherein the functional electrodes are disposed over the membrane.

Example 6

The catheter (14, 214) according to any of examples 1 through 5, further comprising a mechanical guard ring (231), which is located at a proximal side of the reference ring electrode (17, 217) and protrudes outwards from the proximal base section (37, 227) further than the reference ring electrode, and is configured to act as a spacer that blocks contact between reference ring (17, 217) and tissue wall.

Example 7

A system (10) includes a catheter (14), a signal generator (35), an interface (30), and a processor (56). The catheter (14) includes a shaft (44) and an expandable distal-end assembly (28). The shaft has a distal end (44) configured for insertion into a cavity of an organ (12) of a patient (23). The expandable distal-end assembly (28), when expanded, defines an inner volume (77), the distal-end assembly (28) comprising (i) a proximal base section (37) configured to couple the distal-end assembly (28) to a distal end (46) of the shaft (44), (ii) a plurality of functional electrodes (26) that are at least partially external to the inner volume (77) and are configured to be placed in contact with wall tissue of the cavity, and (iii) a reference ring electrode (17) located on the proximal base section (37) of the distal-end assembly (28) externally to the inner volume (77), wherein the reference ring electrode (17) is selectively positioned outside of the inner volume (77) at the base section of the distal-end assembly, and wherein the reference ring electrode (17) is configured to be coupled with each of the plurality of functional electrodes (26) for generating an electric field between each of the plurality of functional electrodes (26) and the ring electrode (17). The signal generator (35) is configured to generate an AC signal between the reference ring electrode (17) and each of the functional electrodes (26). The interface (30) is configured to receive electrical readings between a plurality of the functional electrodes (26) and the reference ring electrode (17). The processor (56) is configured to (i) estimate, from the electrical readings, respective impedances between the functional electrodes (26) and the reference ring electrode (17), and (ii) based on the impedances, estimate, for at least a given functional electrode (26) from among the plurality of functional electrodes (26), a proximity of the functional electrode (26) to the wall tissue.

Example 8

The system (10) according to example 7, wherein the signal generator (35) is configured to generate the AC signal between the reference ring electrode (17, 217) and each of the functional electrodes (26, 226) by generating an electric field between the reference ring electrode (17, 217) and an external surface of each of the functional electrodes (26, 226).

Example 9

The system (10) according to any of examples 7 and 8, wherein the processor (56) is configured to determine that the reference ring electrode (17, 217) is in physical contact with the wall tissue by determining that the measured impedances among the plurality of functional electrodes (26, 226) are all above a given threshold.

Example 10

The system (10) according to any of examples 7 through 9, wherein the processor (56) is configured to estimate the proximity using calibrated proximity data that translates between impedance and electrode-tissue proximity.

Example 11

A method includes inserting an expandable distal-end assembly (28) of a catheter (14) into a cavity of an organ (12) of a patient (23), wherein the distal-end assembly (28) defines an inner volume (77) when expanded, the assembly comprising (i) a proximal base section (37) configured to couple the distal-end assembly to a distal end (46) of a shaft (44) of the catheter, (ii) a plurality of functional electrodes (26) that are at least partially external to the inner volume (77) and are configured to be placed in contact with wall tissue of the cavity, and (iii)

a reference ring electrode (17) located on the proximal base section (37) of the distal-end assembly (28) externally to the inner volume (77), wherein the reference ring electrode is selectively positioned outside of the inner volume at the base section of the distal-end assembly, and wherein the reference ring electrode (17) is configured to be coupled with each of the plurality of functional electrodes (26) for generating an electric field between each of the plurality of functional electrodes and the ring electrode (17). An AC signal is generated between the reference ring electrode (17) and each of the functional electrodes (26). Resulting electrical readings are received, between a plurality of the functional electrodes (26) and the reference ring electrode (17). Respective impedances are estimated, from the electrical readings, between the functional electrodes (26) and the reference ring electrode (17). Based on the impedances, a proximity of the functional electrode to the wall tissue is estimated for at least a given functional electrode (26) from among the plurality of functional electrodes.

Although the examples described herein mainly address cardiac diagnostic applications, the methods and systems described herein can also be used in other medical applications.

It will be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art.

The invention claimed is:

1. A catheter, comprising:

a shaft having a distal end configured for insertion into an anatomical cavity of a patient; and an expandable distal-end assembly that when expanded defines an inner volume, the distal-end assembly comprising:

a proximal base section configured to couple the distal-end assembly to a distal end of the shaft;

a plurality of functional electrodes that are at least partially external to the inner volume and are configured to be placed in contact with wall tissue of the cavity, wherein each of the plurality of functional electrodes comprises an inner electrical insulation coating;

a reference ring electrode located on the proximal base section of the distal-end assembly externally to the inner volume, wherein the reference ring electrode is configured to be coupled with each of the plurality of functional electrodes for generating an electric field between each of the plurality of functional electrodes and the ring electrode; and a mechanical guard ring located on the proximal base section, wherein the mechanical guard ring is configured to prevent the reference ring electrode from contacting the wall tissue.

2. The catheter according to claim 1, wherein the reference ring electrode is fitted on an external perimeter of the proximal base section, and wherein the reference ring electrode is electrically insulated from the base section.

3. The catheter according to claim 1, wherein the distal-end assembly is a basket assembly having an expandable frame comprising multiple splines, and wherein the functional electrodes are coupled to the splines.

4. The catheter according to claim 1, and comprising a far-field electrode located within the inner volume.

5. The catheter according to claim 1, wherein the distal-end assembly is a balloon assembly having an expandable membrane, and wherein the functional electrodes are disposed over the membrane.

6. The catheter according to claim 1, wherein the mechanical guard ring is located at a proximal side of the reference ring electrode and protrudes outwards from the proximal base section further than the reference ring electrode, and is configured to act as a spacer that blocks contact between the reference ring electrode and the tissue wall.

7. A system, comprising:

a catheter, comprising:

a shaft having a distal end configured for insertion into an anatomical cavity of a patient; and an expandable distal-end assembly that when expanded defines an inner volume, the distal-end assembly comprising:

a proximal base section configured to couple the distal-end assembly to a distal end of the shaft;

a plurality of functional electrodes that are at least partially external to the inner volume and are configured to be placed in contact with wall tissue of the cavity, wherein an inner-facing side of each of the plurality of functional electrodes is coated with an insulating coating;

a reference ring electrode located on the proximal base section of the distal-end assembly externally to the inner volume, wherein the reference ring electrode is configured to be coupled with each of the plurality of functional electrodes for generating an electric field between each of the plurality of functional electrodes and the ring electrode; and a protruding guard ring located at a proximal side of the reference ring electrode;

a signal generator configured to generate an AC signal between the reference ring electrode and each of the functional electrodes;

an interface configured to receive electrical readings between a plurality of the functional electrodes and a reference ring electrode; and a processor, which is configured to:

estimate, from the electrical readings, respective impedances between the functional electrodes and the reference ring electrode; and based on the impedances, estimate, for at least a given functional electrode from among the plurality of functional electrodes, a proximity of the functional electrode to the wall tissue.

8. The system according to claim 7, wherein the signal generator is configured to generate the AC signal between the reference ring electrode and each of the functional electrodes by generating an electric field between the reference ring electrode and an external surface of each of the functional electrodes.

9. The system according to claim 7, wherein the processor is configured to determine that the reference ring electrode is in physical contact with the wall tissue by determining that the measured impedances among the plurality of functional electrodes are all above a given threshold.

10. The system according to claim 7, wherein the processor is configured to estimate the proximity using calibrated proximity data that translates between impedance and electrode-tissue proximity.

11. A method, comprising:

inserting an expandable distal-end assembly of a catheter into a cavity of an organ of a patient, wherein the distal-end assembly defines an inner volume when expanded, the assembly comprising:

a proximal base section configured to couple the distal-end assembly to a distal end of a shaft of the catheter;

a plurality of functional electrodes that are at least partially external to the inner volume and are configured to be placed in contact with wall tissue of the cavity, wherein each of the plurality of functional electrodes comprises a coating configured to minimize contact between an inner surface of the electrode and a patient's blood; and a reference ring electrode located on the proximal base section of the distal-end assembly externally to the inner volume, wherein the reference ring electrode is configured to be coupled with each of the plurality of functional electrodes for generating an electric field between each of the plurality of functional electrodes and the ring electrode;

generating an AC signal between the reference ring electrode and each of the functional electrodes such that an electric field is generated between the reference ring electrode and each of the functional electrodes, wherein the coating of the plurality of electrodes reduces a path of the electric field through the inner volume and increases a path of the electric field directed outwardly across the wall tissue;

receiving resulting electrical readings between a plurality of the functional electrodes and the reference ring electrode;

estimating, from the electrical readings, respective impedances between the functional electrodes and the reference ring electrode; and based on the impedances, estimating, for at least a given functional electrode from among the plurality of functional electrodes, a proximity of the functional electrode to the wall tissue.

12. The method according to claim 11, wherein generating the AC signal between the reference ring electrode and each of the functional electrodes comprises generating an electric field between the reference ring electrode and an external surface of each of the functional electrodes.

13. The method according to claim 11, further including determining that the reference ring electrode is in physical contact with the wall tissue such that the measured impedances among the plurality of functional electrodes are all above a given threshold.

14. The method according to claim 11, wherein estimating the proximity comprises using calibrated proximity data that translates between impedance and electrode-tissue proximity.

15. The method according to claim 11, wherein the reference ring electrode is fitted on an external perimeter of the proximal base section, and wherein the reference ring electrode is electrically insulated from the base section.

16. The method according to claim 11, wherein the distal-end assembly is a basket assembly having an expandable frame comprising multiple splines, and wherein the functional electrodes are coupled to the splines.

17. The method according to claim 11, wherein the distal-end assembly is a balloon assembly having an expandable membrane, and wherein the functional electrodes are disposed over the membrane.

18. The method according to claim 11, and comprising, using a mechanical guard ring, which is located at a proximal side of the reference ring electrode and protrudes outwards from the proximal base section further than the reference ring electrode, blocking contact between the reference ring electrode and the tissue wall.

19. The catheter according to claim 1, wherein the inner electrical insulation coating is configured to minimize contact between blood and the plurality of functional electrodes upon contact with the wall tissue of the cavity.

20. The system according to claim 8, wherein the insulating coating is configured to reduce a path of the electric field through the inner-facing side of each of the plurality of functional electrodes.

* * * * *